United States Patent
Park et al.

(10) Patent No.: US 9,364,183 B2
(45) Date of Patent: Jun. 14, 2016

(54) HAPTIC GLUCOMETER GUIDE

(71) Applicants: Jacob Park, Richmond, VA (US); Matthew Standard, Manassas, VA (US); Dianne Pawluck, Richmond, VA (US); Linda Thurby-Hay, Richmond, VA (US); John Clore, Richmond, VA (US); Amber Spain, Richmond, VA (US)

(72) Inventors: Jacob Park, Richmond, VA (US); Matthew Standard, Manassas, VA (US); Dianne Pawluck, Richmond, VA (US); Linda Thurby-Hay, Richmond, VA (US); John Clore, Richmond, VA (US); Amber Spain, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/596,262

(22) Filed: Jan. 14, 2015

(65) Prior Publication Data

US 2015/0196254 A1    Jul. 16, 2015

Related U.S. Application Data

(60) Provisional application No. 62/076,241, filed on Nov. 6, 2014, provisional application No. 61/927,314, filed on Jan. 14, 2014.

(51) Int. Cl.
    *A61B 5/00* (2006.01)
    *A61B 5/157* (2006.01)
    *A61B 5/15* (2006.01)
    *A61B 5/145* (2006.01)
    *A61B 5/151* (2006.01)
    *A61F 4/00* (2006.01)

(52) U.S. Cl.
    CPC ............ *A61B 5/702* (2013.01); *A61B 5/1411* (2013.01); *A61B 5/150022* (2013.01); *A61B 5/150358* (2013.01); *A61B 5/150748* (2013.01); *A61B 5/150801* (2013.01); *A61B 5/14532* (2013.01); *A61B 5/6826* (2013.01); *A61F 4/00* (2013.01)

(58) Field of Classification Search
    CPC .. A61B 5/150748; A61B 5/702; A61B 5/151; A61B 5/157; A61B 5/150358; A61B 5/1411; A61B 5/15002; A61B 5/150801
    USPC .......................................... 422/544; 600/365
    See application file for complete search history.

(56) References Cited

U.S. PATENT DOCUMENTS

| | | | |
|---|---|---|---|
| 5,786,584 A * | 7/1998 | Button et al. | 235/462.15 |
| 6,626,851 B2 * | 9/2003 | Hirao et al. | 600/576 |
| 2006/0034728 A1 * | 2/2006 | Kloepfer et al. | 422/68.1 |
| 2006/0161078 A1 * | 7/2006 | Schraga | 600/583 |
| 2010/0261988 A1 * | 10/2010 | Tamir | A61B 5/1411 600/365 |
| 2014/0019139 A1 | 1/2014 | Abulhaj et al. | |
| 2014/0257066 A1 * | 9/2014 | Suess | A61B 5/150748 600/365 |

* cited by examiner

*Primary Examiner* — Jill Warden
*Assistant Examiner* — Jacqueline Brazin
(74) *Attorney, Agent, or Firm* — Whitham Curtis Christofferson & Cook, PC

(57) ABSTRACT

A glucometer guide is provided to address the difficulty that blind or visually impaired diabetic patients have when attempting to independently use a glucometer. The guide provides haptic cues for the effective transfer of blood onto a test strip.

7 Claims, 4 Drawing Sheets

HAPTIC GLUCOMETER GUIDE

CROSS-REFERENCE TO RELATED APPLICATIONS

This application claims the priority of U.S. Provisional Patent Application Nos. 61/927,314 and 62/076,241.

FIELD OF THE INVENTION

Embodiments of the invention provide a haptic glucometer guide that allows visually-impaired patients to independently and accurately obtain blood glucose readings.

BACKGROUND OF THE INVENTION

For a non-blind patient with diabetes, the process of taking a blood sample with a glucometer is relatively easy due to their ability to visually guide themselves through each step: choosing a place to pierce the skin, lancing that chosen point, and then ensuring that the blood gained from lancing the skin is able to be appropriately placed on a glucometer test strip.

Poorly-managed diabetes can result in diabetic retinopathy which causes gradual loss of an individual's retinal field, thus there can be a correlation between diabetes and blindness. Other diabetics may be blind by other means. A blind or otherwise visually impaired diabetic can easily choose a point on their person to use as a testing site and lance that point, but a problem arises when the visually impaired diabetic is unable to find that miniscule spot again and align it properly with a small test strip so that the blood is drawn into the test strip. There are some simple methods that the blind or visually impaired diabetic can use to find the spot again, such as trying to line up the end of the test strip with the specific area based on memory, or using an ad-hoc home-made method that orients and places the test strip in the same direction that the lancet was pointed. However, those home-made and mental memory solutions do not guarantee that the blood will get to the test strip, and the use of those methods will most likely result in smearing the blood sample into the skin test site until it is either too small to use or it is impure, leading to inaccurate readings or the need for another lancet piercing.

Blind or otherwise visually impaired diabetic patients often waste many test strips attempting to obtain one valid blood glucose reading. These individuals usually require assistance from others when measuring their blood glucose levels or they risk wasting expensive test strips for which only a certain amount are provided each week by insurance companies.

There are devices on the market that perform both lancing and testing in an automated fashion. However these devices, such as the Gio glucometer (Eric Forman Gio glucometer), do not integrate the lancing and testing steps and rely on the user to visually guide a blood sample onto a test strip. Electronic glucose meters featuring synthesized speech, such as The Prodigy Voice Blood Glucose Meter, are intended for use by visually impaired diabetics by informing the user of the resulting numeric measurement through audio cues (U.S. patent application Ser. No. 13/547,400). However, users of these devices still cannot successfully coordinate the transfer of blood to the test strip without excessive blood drawing or external assistance.

SUMMARY OF THE INVENTION

The haptic glucometer guide, according to embodiments of the invention, is a device that assists the blind or visually impaired subject in measuring their blood glucose levels with a glucometer. In some embodiments, the subject has diabetes.

Hence, it is an object of the invention to serve in guiding the visually impaired diabetic in taking and monitoring their glucose levels without assistance from others or wasting test strips. It is an object of the invention to: (a) provide a fixed alignment and rotational angle between the finger prick created by the lancet and the test strip, (b) allow the user to then rotate the finger to place the blood drop on the test strip, and (c) provide a compartment for the attachment of a glucometer and maintain the correct positional relationship between the lancet seat and the glucometer test strip.

The guide is preferably manufactured with dimensions allowing for its use with any standard glucometer. The guide facilitates the use of a glucometer for the purposes of testing blood sugar by placing the desired test site, preferably a subject's finger, onto a specified location on the guide, the top window where lancing occurs. After lancing, the user rotates the test site so that the blood will be drawn into the test strip to the glucometer.

In an exemplary embodiment, the user inserts a test strip into the guide with a glucometer already secured into the device. The user then places a finger inside the cylindrical cavity and pricks their finger at the desired location via the window on the top face of the cylindrical section. The user then rotates their finger along the inside of the cylindrical section with the prick site travelling down the open window. The bead of blood makes contact with the test strip, which is positioned at the bottom of the window, and the glucometer records and communicates the results to the user.

Additional features and advantages of the invention will be set forth in the description below, and in part will be apparent from the description, or may be learned by practice of the invention. The advantages of the invention can be realized and attained by the exemplary structure particularly pointed out in the written description and claims hereof as well as the appended drawings.

DETAILED DESCRIPTION

Embodiments of the invention provide a glucometer guide comprising:
 a compartment for connection to a glucometer;
 a cavity formed to accommodate an inserted finger of a user
  and permit rotation of the finger therein; and
 a window in said cavity wherein the window is positioned
  to allow a lancet to prick the finger through the window and to allow the blood of the pricked finger to contact a test strip after rotation of the finger, wherein the test strip extends between the window in the cavity and the glucometer in the compartment.

Figure 1A:
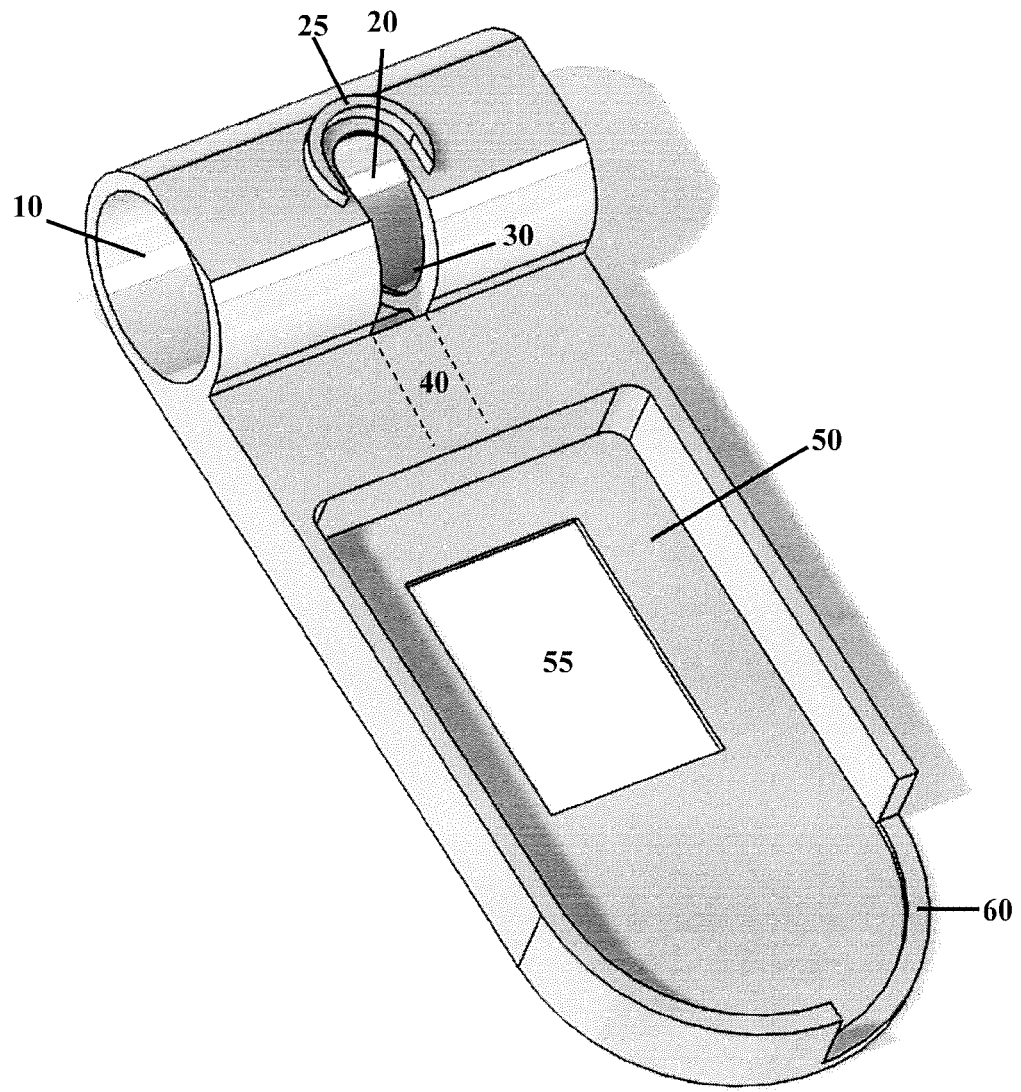
FIG. 1A. Isometric view of an exemplary glucometer guide illustrating the opening for the finger hole 10, top window 20 where lancing occurs containing a raised lancet seat 25, bottom window where the blood contacts the test strip 30, positioning of the test strip 40, compartment for glucometer 50 containing an opening 55 on the bottom, and a cutout for a USB port and/or audio jack 60.
Figure 1B:
FIG. 1B. Side profile view of the side of the glucometer guide of FIG. 1A.
Figure 1C:
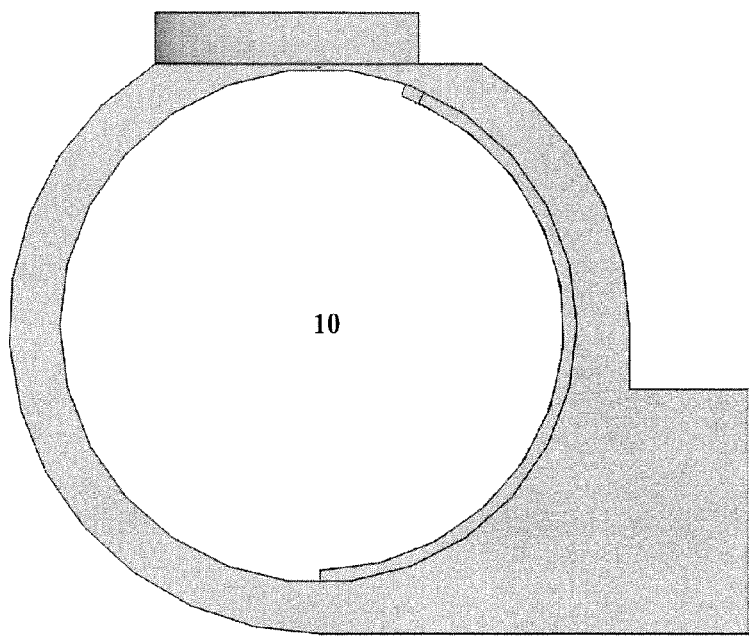
FIG. 1C. Enlarged side view of the glucometer guide showing the finger cavity 10.

FIG. 1A-E illustrate an exemplary embodiment of the haptic glucometer guide. In FIG. 1A, the guide includes a finger hole 10 member and a compartment member 50. The finger hole 10 is sized to accommodate the finger of a subject. In some embodiments, the finger hole will be sized for the average adult (or average adult female or average adult male), while in other embodiments, the finger hole can be sized for the average toddler, child or young adult. The finger hole 10 is preferably cylindrical or multipolygonal so that any part of the finger can be used (e.g., from distal to proximal locations and at any rotation of the finger). In addition, the finger hole 10 can be sized for easy use with any of the user's fingers.

An advantage of the haptic glucometer guide is that a glucometer (not shown) can be affixed to the guide in the compartment 50 so that only one hand is required for holding the glucometer and guide. In the embodiment shown in FIG. 1A, the compartment 50 is a depression in a plastic or ceramic housing which is sized to accommodate any of a variety of commercially available glucometers; however, it will be recognized that there are other mechanisms for connecting the guide and the glucometer. The configuration shown in FIGS. 1A-E would work well with the Prodigy Voice Blood Glucose Meter, a blood glucose meter intended for use by visually impaired diabetics which provides audio cues indicative of numeric measurements and other useful features for the diabetic patient; however, the haptic glucometer guide can be configured for optimal use with other glucometers and/or may be universal in character to allow use with a wide variety of glucometers (e.g., parameters such as the size and shape of the compartment 50 can be varied and/or made adjustable). In a preferred embodiment, the haptic glucometer guide is made from thermoplastic materials (e.g., ABS, polypropylene, etc.) and can be manufactured by three dimensional printing, injection molding, etc.

In the embodiment shown in FIG. 1A, there is a cutout opening 60 in the compartment 50 end which will allow for connecting the glucometer to a USB port, power cord, audio jack or other device. In addition, there is an opening 55 in the base of the compartment 50 (see also FIG. 1E). This opening 55 may serve the simple function of allowing the user to more easily push the glucometer out of the compartment 50. However, the opening 50 may also permit various features of the glucometer to be accessed. For example, a display, Braille provisioning port, audio output, etc. of the glucometer might be accessible through the opening 55.

FIG. 1A illustrates an elongated opening having a top window portion 20 and a side window portion 30 in the finger hole compartment. Upon insertion of the person's finger in the finger hole 10, a lancet can be plunged downward to a target site in the finger from which to draw blood. A lancet seat 25 can be used to help the person guide the lancet to the desired target site. Preferably the lancet seat 25 is raised above the top window portion 20 as shown in FIG. 1A so as to enable a blind person to more easily locate the lancet and the target site. In some embodiments, the lancet seat 25 can be adjustable to accommodate different types of lancets. Upon pricking the finger at the target site, the finger can simply be rotated, e.g., preferably 90° (but a range of, for example 45° to 135° might also be employed) so that the blood can contact a test strip (not shown) which extends from the lower window portion 30 to the glucometer in the compartment 50 at region 40.

An advantage of the haptic glucometer guide is that it allows the user to easily align test strips with the pricked target site and allows the glucometer to make the readings. This can be accomplished by having the test strip extend from the glucometer in the compartment 50 to or into the lower window portion opening 30. A blind person (or other user of the haptic glucometer guide) can easily locate the lower window portion 30 because it is an opening in the finger hole portion of the guide (e.g., it can be located by feel). This lower window portion 30 will be aligned with the measurement portion of the glucometer. Preferably, as shown in FIG. 1A, the region 40 is on a raised portion of the housing above the depression made from the compartment so as to support the test strip. However, further non-visual cues or alignment features can be built in at region 40 by, for example, including dimples, striations, a slight depression, a slight bulge, etc. to alert the visually impaired as to the location of region 40. In operation, after pricking the finger at the target site, the finger is simply rolled to allow the blood to contact the test strip at region 40 so that results can be read by the glucometer. The haptic glucometer guide can therefore result in easier operation by, for example, the visually impaired (e.g., they can more easily make measurements without the assistance of others), and can result in a significant reduction in wasted test strips (thus a cost savings).

Figure 1D:
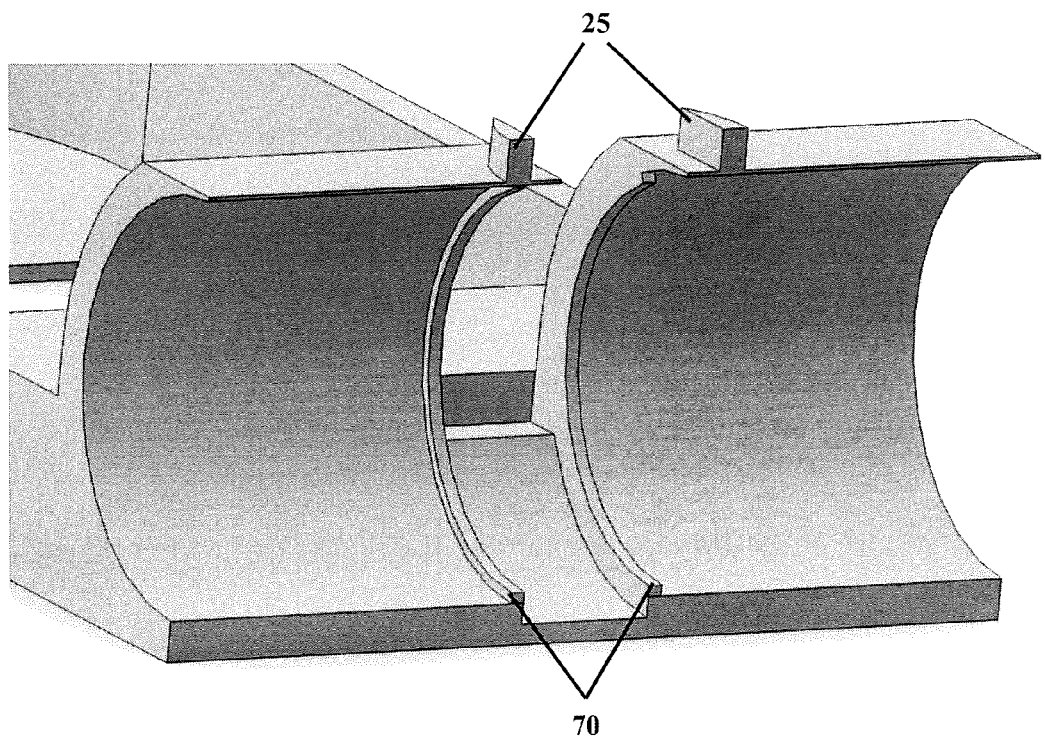
FIG. 1D. Section view of the finger cavity illustrated in FIGS. 1A-1C. Haptic cues such as raised ridges 70, one or more dimples (not shown) and/or a sunken area (not shown) may be positioned to provide guidance during finger rotation and to ensure that blood does not contact the glucometer.
Figure 1E:
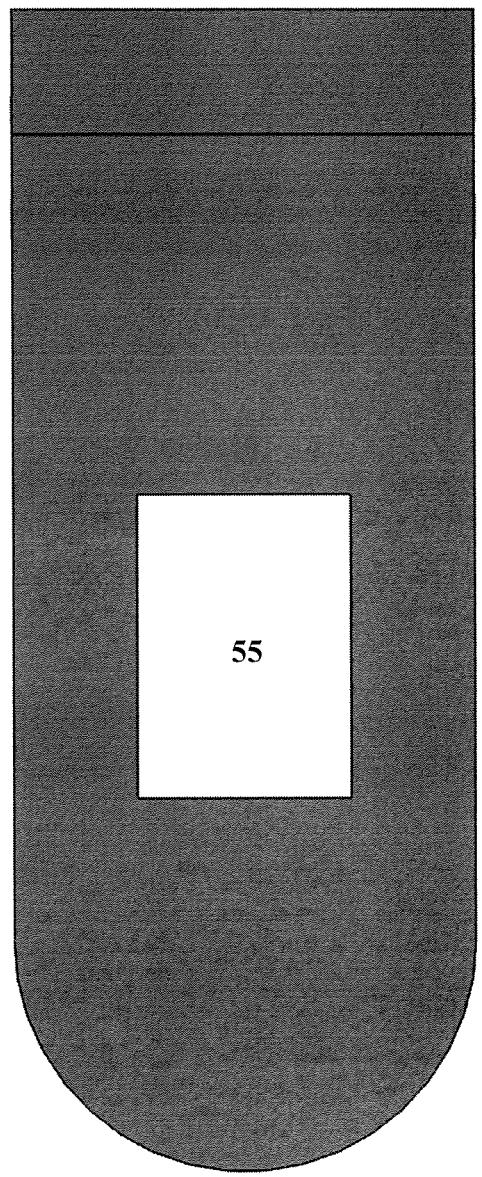
FIG. 1E. Bottom view of the haptic glucometer guide.

FIG. 1D (and FIGS. 1B and 1C) illustrate an exemplary feature of the haptic glucometer guide which aids in alignment. Specifically, in FIG. 1D there is shown two elongated, inwardly projecting ridges 70 on either side of the window opening. These ridges project into the finger hole 10 and can be felt by the user when locating a portion of his or her finger to be pricked by the lancet. While two ridges 70 are shown, a single ridge on one side of the window opening could be used. Alternatively, a series of dimples (inward or outwardly projecting) could be aligned with one or both sides of the window, or even a single dimple adjacent the window could be utilized. Bumps or other haptic cues may also function in the same way as the ridges 70.

Other advantages of having the guide secured to a glucometer may include providing feedback to the user when tests are successfully made. For example, a speaker in the glucometer may alert the user when the test is successfully completed as well as the results of the test (and or other information of interest), or the glucometer may be equipped with a shaker so that after the test is successfully completed the combination of the glucometer and the guide can be vibrated to let the user know that the test has been successful, etc.

Embodiments of the invention also provide a method for the measurement of blood glucose in a subject comprising analyzing a blood sample with a glucometer inserted into a glucometer guide as described herein. In exemplary embodiments, the subject has diabetes. In some embodiments, the glucometer guide of the invention is used by blind or visually impaired individuals to measure their own blood glucose levels. In some embodiments, the guide is used by individuals who are not blind or visually impaired, but who would still benefit from the use of a guide as described herein, such as elderly or adolescent individuals. In some embodiments, the guide is used as a simple tool for medical practitioners or those otherwise assisting the individual to quickly and easily obtain blood glucose levels from the individual.

The glucometer guide of the invention reduces the task of transferring blood to a test strip to one wrist rotation guided by haptic cues inside the cylindrical cavity 10 of the guide where the finger is placed (FIG. 1A-D).

In some methods of the present invention, a glucometer is turned on and a test strip is inserted into the glucometer. The glucometer, with the test strip inserted, is placed into the fitted compartment 50 of the assistive device. Alternatively, the test strip may be inserted after the glucometer is fitted into the device. The test strip sits on the shelf at region 40 between the glucometer compartment 50 and the finger hole 10. The user places a finger through either end of the circular finger hole and aligns the desired test site on their finger with the top window 20 of the circular cavity. The user then places a loaded and cocked lancet device at the top window 20 of the guide with their other hand, where the inserted finger is positioned, and then triggers the lancet device. Once pierced, the user rotates their finger 90 degrees along the open slot until they feel the test strip at the bottom window portion 30, and slightly rotates the finger up and down while maintaining contact with the test strip until, for example, audio cues from the glucometer let the user know that the blood sample was collected and analyzed successfully. In some embodiments, although the user feels the test strip, the bead of blood, and not the finger, is what contacts the test strip. Confirmation of the sample is almost instantaneous with some glucometers and the user is given an audio cue that the user has reached the correct orientation and the sample was taken. Glucometers that are used with the guide may also use feedback other than or in combination with audio cues such as vibrotactile feedback. For example, the glucometer may vibrate when the sample has been received or analyzed.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A glucometer guide comprising:
    a compartment at a first end of the guide for connection to a glucometer;
    a cavity formed at a second end of the guide to accommodate an inserted finger of a user and permit rotation of the finger therein,
    the guide having a longitudinal axis extending between the first end and the second end;
    the cavity being a substantially hollow cylindrical cavity having its longitudinal axis extending perpendicular to the longitudinal axis of the guide;
    a window in said cavity
    wherein the window is positioned to allow a lancet to prick the finger through said window and to allow the blood of the pricked finger to contact a test strip after rotation of the finger,
    wherein the window is positioned to allow contact with an end of the test strip extending between the window in the cavity and the glucometer when housed in the compartment,
    wherein the guide is a one-piece device, and
    wherein said compartment is configured for removably attaching said glucometer to the guide.

2. The guide of claim 1, further comprising a shelf for positioning of the test strip between the window in the cavity and the glucometer in the compartment.

3. The guide of claim 2, further comprising an alignment feature on said shelf.

4. The guide of claim 1, further comprising an opening at the bottom of said compartment.

5. A method for the measurement of blood glucose in a subject, the method comprising:
    analyzing a blood sample with a glucometer using a glucometer guide,
    wherein said guide having a longitudinal axis extending between a first end and a second end comprises:
    a compartment at the first end of the guide for connection to the glucometer;
    a cavity formed at the second end of the guide to accommodate an inserted finger of a user and permit rotation of the finger therein;
    the cavity being a substantially hollow cylindrical cavity having its longitudinal axis extending perpendicular to the longitudinal axis of the guide;
    a window in said cavity wherein the window is positioned to allow a lancet to prick the finger through said window and to allow the blood of the pricked finger to contact a test strip after rotation of the finger,
    wherein the test strip extending between the window in the cavity and the glucometer in the compartment,
    wherein the guide is a one-piece device and wherein said compartment is configured for removably attaching said glucometer to the guide, and
    wherein the step of analyzing includes
    connecting the glucometer to the compartment of the glucometer guide;
    inserting a finger into the cavity of the glucometer guide;
    pricking the finger with the lancet through the window in the cavity;
    rotating the finger in the cavity until the blood of the pricked finger contacts the test strip extending between the window in the cavity and the glucometer in the compartment; and measuring the blood glucose of the blood sampled on the test strip with the glucometer.

6. A glucometer guide comprising:

a compartment at a first end of the guide for connection to a glucometer;

a cavity formed at a second end of the guide to accommodate an inserted finger of a user and permit rotation of the finger therein;

the guide having a longitudinal axis extending between the first end and the second end;

the cavity being a substantially hollow cylindrical cavity having its longitudinal axis extending perpendicular to the longitudinal axis of the guide;

a window in said cavity wherein the window is positioned to allow a lancet to prick the finger through said window and to allow the blood of the pricked finger to contact a test strip after rotation of the finger, wherein the window is positioned to allow contact with an end of the test strip extending between the window in the cavity of the glucometer when housed in the compartment;

at least one protrusion adjacent to said window and extending into the cavity;

wherein the guide is a one-piece device; and wherein said compartment is configured for removably attaching said glucometer to the guide.

7. The guide of claim 6, wherein said at least one protrusion includes a pair of elongated, inwardly projecting ridges positioned on opposite sides of said window.

\* \* \* \* \*